United States Patent
Kim et al.

(10) Patent No.: US 10,060,063 B2
(45) Date of Patent: *Aug. 28, 2018

(54) LAUNDRY MACHINE AND CONTROLLING METHOD OF THE SAME

(71) Applicant: LG ELECTRONICS INC., Seoul (KR)

(72) Inventors: Pyoung Hwan Kim, Gyeongsangnam-do (KR); Su Hee Shin, Gyeongsangnam-do (KR); Seong Hae Jeong, Gyeongsangnam-do (KR); Young Soo Kim, Gyeongsangnam-do (KR); Deug Hee Lee, Gyeongsangnam-do (KR)

(73) Assignee: LG ELECTRONICS INC., Seoul (KR)

( * ) Notice: Subject to any disclaimer, the term of this patent is extended or adjusted under 35 U.S.C. 154(b) by 79 days.

This patent is subject to a terminal disclaimer.

(21) Appl. No.: 15/187,098

(22) Filed: Jun. 20, 2016

(65) Prior Publication Data

US 2016/0298278 A1     Oct. 13, 2016

Related U.S. Application Data

(63) Continuation of application No. 14/017,925, filed on Sep. 4, 2013, now Pat. No. 9,382,652, which is a (Continued)

(30) Foreign Application Priority Data

Sep. 8, 2006   (KR) .................. 10-2006-0086653

(51) Int. Cl.
  *D06F 35/00* (2006.01)
  *D06F 39/00* (2006.01)
  (Continued)

(52) U.S. Cl.
  CPC ............ *D06F 35/005* (2013.01); *D06F 35/00* (2013.01); *D06F 39/008* (2013.01);
  (Continued)

(58) Field of Classification Search
  CPC ...... D06F 35/00; D06F 35/005; D06F 39/008; D06F 2214/00; D06F 2220/00; D06F 2204/04
  See application file for complete search history.

(56) References Cited

U.S. PATENT DOCUMENTS

| 5,122,158 A | 6/1992 | Kuroda et al. |
| RE39,304 E | 9/2006 | Kasen et al. |

(Continued)

FOREIGN PATENT DOCUMENTS

| CN | 1537995 A | 10/2004 |
| EP | 1489217 A1 | 12/2004 |

(Continued)

OTHER PUBLICATIONS

Ji He et al., "The Relationship Between Breeding Conditions of Dust Mites in College Students' Dormitory and Allergic Asthma", Chinese Journal of School Health, vol. 25, issue 4, Aug. 31, 2004.

*Primary Examiner* — Joseph L Perrin
(74) *Attorney, Agent, or Firm* — Dentons US LLP

(57) ABSTRACT

The present invention relates to a laundry machine and a controlling method, which can remove allergens on the laundry. A controlling method of a laundry machine includes a mite-killing step of supplying seam to a drum to make laundry exposed to a hot environment at or over a temperature and for or over a duration of time, wherein the temperature and the duration are predetermined enough to kill house dust mites on the laundry; a rinsing step of rinsing the laundry; and a spin-drying step of spin-drying the rinsed laundry. The present invention has an advantageous effect of (Continued)

removing allergens including house dust mites, animal hair and pollens efficiently. In addition, if the house dust mites are killed by using steam, energy efficiency is high and an effect of mite-killing is great.

20 Claims, 7 Drawing Sheets

Related U.S. Application Data continuation of application No. 11/920,355, filed as application No. PCT/KR2007/004349 on Sep. 7, 2007, now Pat. No. 8,601,627.

(51) Int. Cl.
*D06F 39/08* (2006.01)
*A01M 7/00* (2006.01)
*A61L 2/20* (2006.01)
*D06F 23/02* (2006.01)

(52) U.S. Cl.
CPC .......... *D06F 39/085* (2013.01); *D06F 39/087* (2013.01); *A01M 7/0089* (2013.01); *A61L 2/20* (2013.01); *D06F 23/02* (2013.01); *D06F 2204/04* (2013.01); *D06F 2214/00* (2013.01); *D06F 2220/00* (2013.01)

(56) References Cited

U.S. PATENT DOCUMENTS

| | | |
|---|---|---|
| 2001/0039684 A1 | 11/2001 | Kasper et al. |
| 2004/0237603 A1 | 12/2004 | Kim et al. |
| 2004/0255983 A1 | 12/2004 | McKeon ............... A61L 2/02 134/26 |
| 2006/0101586 A1 | 5/2006 | Park et al. |
| 2006/0151005 A1 | 7/2006 | Kim et al. |
| 2007/0169282 A1 | 7/2007 | Kim |
| 2007/0283726 A1 | 12/2007 | Lee ................. D06F 37/203 68/12.06 |
| 2008/0092602 A1 | 4/2008 | Quddus et al. |

FOREIGN PATENT DOCUMENTS

| | | |
|---|---|---|
| EP | 1681384 A1 | 7/2006 |
| JP | 58012697 A | 1/1983 |
| JP | 2198595 A | 8/1990 |
| JP | 2006141985 A | 6/2006 |
| KR | 100162354 B | 1/1999 |
| KR | 1020050098162 A | 10/2005 |
| KR | 1020050113950 A | 12/2005 |
| KR | 1020050113952 A | 12/2005 |
| KR | 1020060019982 A | 3/2006 |
| KR | 1020060082689 A | 7/2006 |
| RU | 2083226 C1 | 7/1997 |
| WO | 2005115095 A2 | 12/2005 |
| WO | 2006090973 A1 | 8/2006 |

[Figure 1]
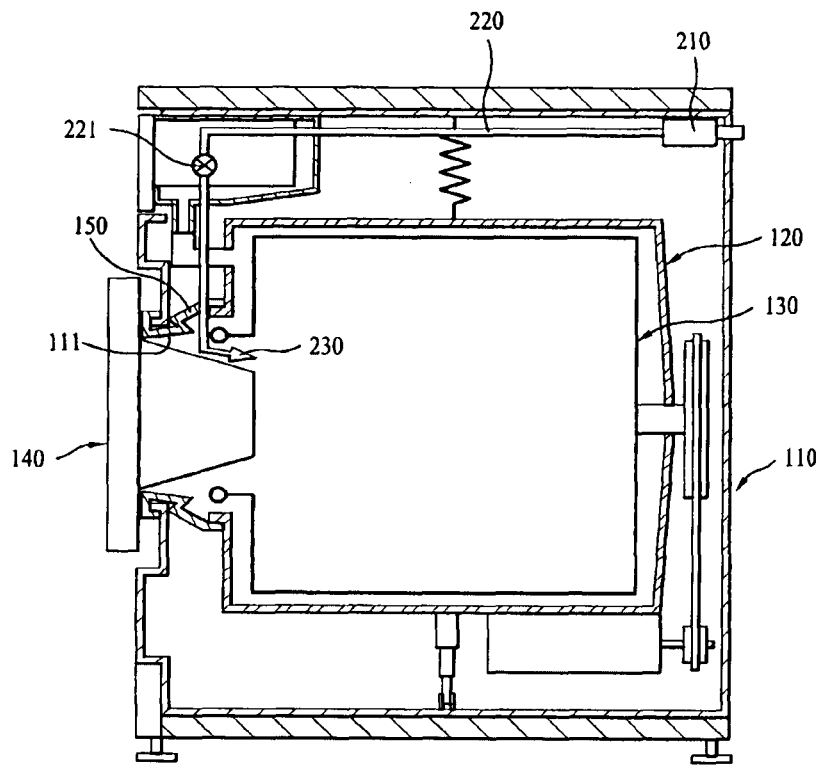
[Figure 2]
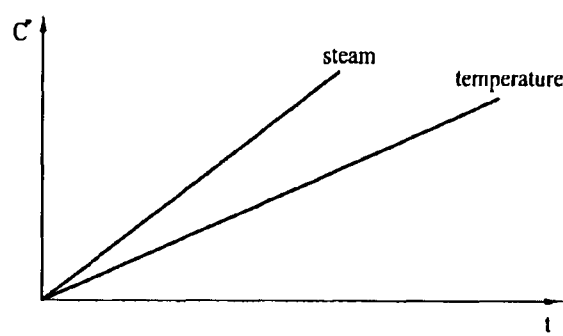

[Figure 3]
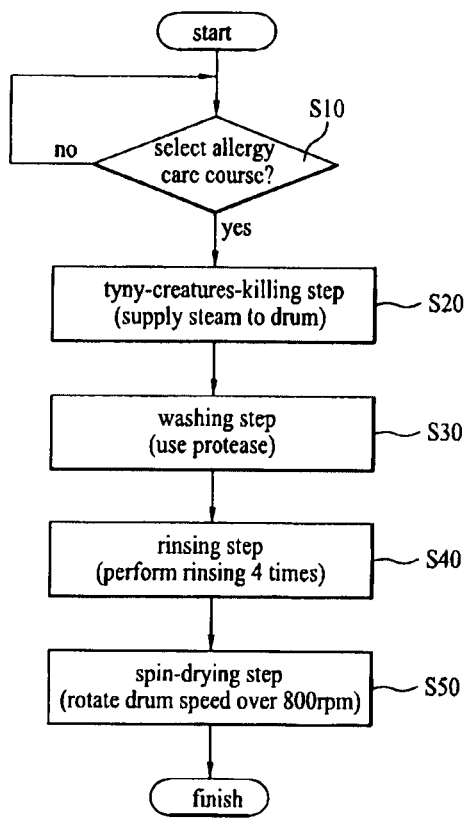

【Figure 4】
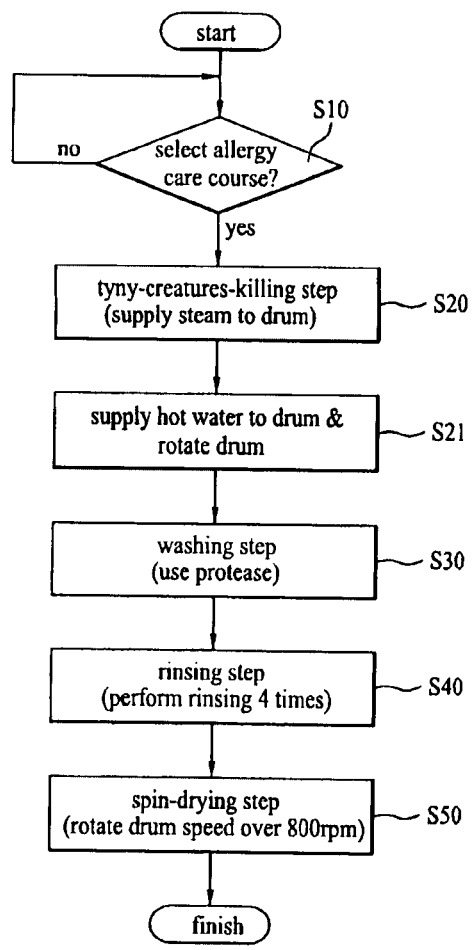

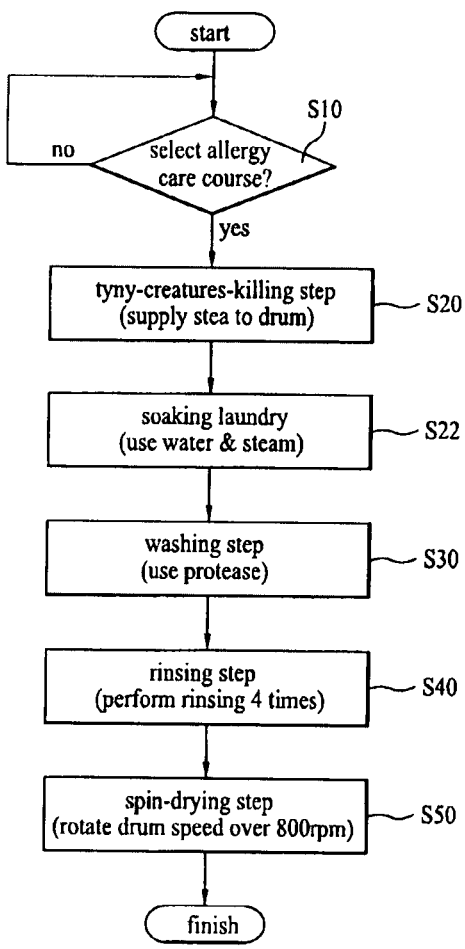
[Figure 5]

[Figure 6]
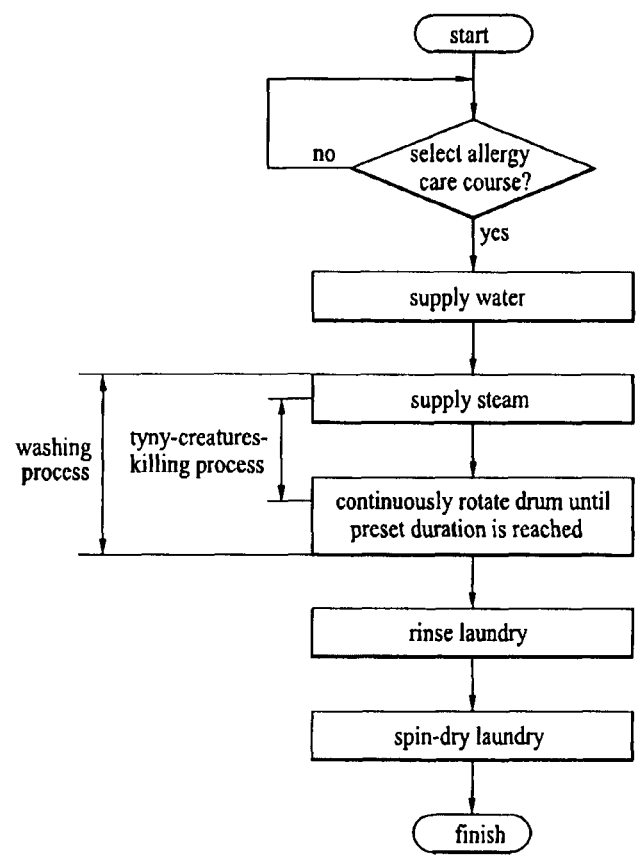

[Figure 7]
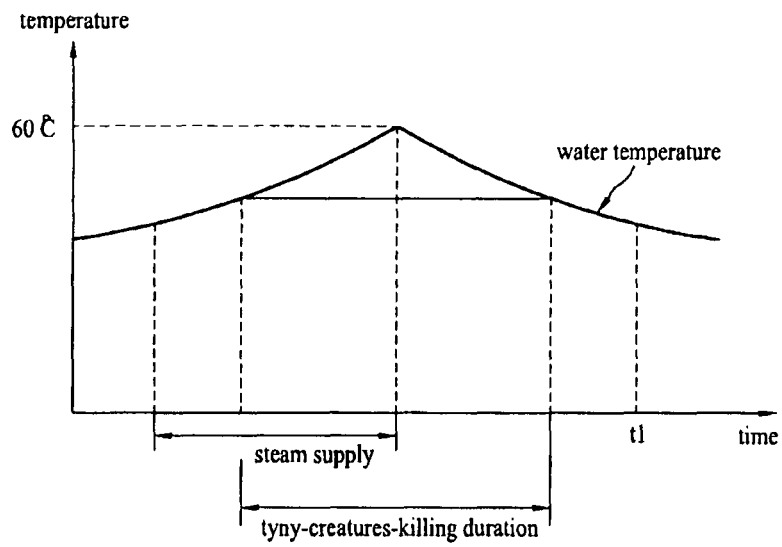
[Figure 8]
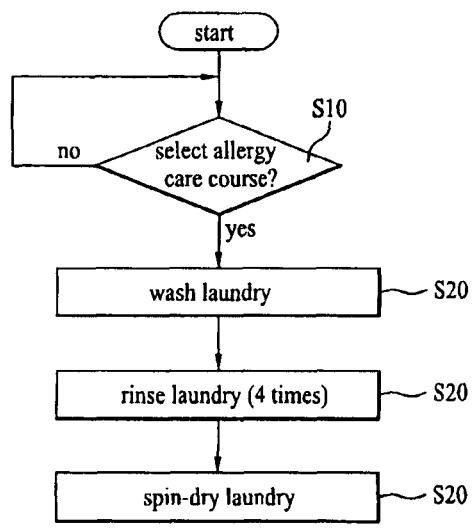

[Figure 9]

| Sample | Cat allergen, Fel d1 (mU/g) |
|---|---|
| unwashed 1 | 9827 |
| unwashed 2 | 9086 |
| unwashed 3 | 11709 |
| washed 1 | < min |
| washed 2 | < min |
| washed 3 | < min |

[Figure 10]

| Sample | Brich pollen allergen, Bet v1 (μg/g) |
|---|---|
| unwashed 1 | 9827 |
| unwashed 2 | 9086 |
| unwashed 3 | 11709 |
| washed 1 | < min |
| washed 2 | < min |
| washed 3 | < min |

LAUNDRY MACHINE AND CONTROLLING METHOD OF THE SAME

This application is a continuation of U.S. application Ser. No. 14/017,925, filed on Sep. 4, 2013, now allowed, which is a continuation of U.S. application Ser. No. 11/920,355, filed on Dec. 8, 2009, which is a national stage application of PCT/KR2007/004349, filed on Sep. 7, 2007, and claims priority from Korean Application No: 10-2006-0086653, filed Sep. 8, 2006, all of which are incorporated by reference in their entirety herein.

TECHNICAL FIELD

The present invention relates to a laundry machine. Laundry machines may include laundry washers and laundry dryer. Typically, laundry washers are categorized into pulsator type washers and drum type washers. Also, there are washers having a drying function which can perform drying as well as washing.

BACKGROUND ART

There are conventional laundry machines including steam generators. In case of laundry washers, washing efficiency is remarkably enhanced by using steam to perform washing.

FIG. 1 shows a drum type washer as an example of a conventional laundry machine.

The drum type washer shown in FIG. 1 includes a body 110, a tub 120, a drum 130 and a steam generator.

Here, the body 110 defines an exterior appearance of the drum type washer and the tub 120 is supportably provided within the body 110.

The drum 130 is rotatable in the tub 120 and an opened portion of the drum 130 is positioned toward an opening 111 formed in the body 110.

A door 140 is coupled to the opening 111 of the body 110 to open and close the opening 111. A rim 150 is coupled to an inner circumference of the opening 111 to close airtight between the door 140 and the opening 111.

In addition, a plurality of through-holes may be formed around a circumferential surface of the drum 130 and not only wash water but also steam may pass the through-holes into the drum 130.

The steam generator is employed to supply a predetermined amount of steam to the drum 130.

Such steam generator evaporates water into high temperature hot steam and supplies the hot steam to the drum 130.

The steam generator includes a heating part 210 and a steam supply pipe 220. The heating part 210 evaporates water into high temperature steam and the steam supply pipe 220 forms a steam path to allow the steam evaporated by the heating part 210 to be supplied to the drum 130.

The steam generator further includes a spray nozzle 230 to spray the steam flowing in the steam supply pipe 220 into the drum 130.

The spray nozzle 230 is nozzle-shaped to spray the steam smoothly and an outlet end of the nozzle 230 is toward an inside of the drum 130.

The spray nozzle 230 may be provided to spray steam directly into the drum 130 or into the tub 120, depending on cases. Here, the steam sprayed into the tub 120 may be supplied to the drum 130 through the through-holes.

DISCLOSURE

Technical Problem

The above conventional laundry washer is controlled to use steam, especially, to perform soaking or sterilization of laundry by using steam so that washing efficiency is enhanced.

Steam has been used to soak or sterilize laundry in the conventional laundry washers and the steam is supplied only enough to perform those functions.

Recently, there have been increasing patients suffering atopic dermatitis that is one of environmental diseases. Allergens including house dust mites and their excretions, animal hair including cat and dog hair and pollens may aggravate atopic dermatitis.

If people not suffering atopic dermatitis are exposed to those allergens consistently, they may end up with dermatitis.

Especially on mattress covers, bed covers, pillow covers, sheets, sofa covers, cushion covers and floor cushion covers are parasitic a lot of mites or animal hair. Those allergens cannot be removed in the conventional laundry washing method efficiently.

Technical Solution

To solve the problems, an object of the present invention is to provide a laundry machine and a controlling method, which can remove allergens efficiently from the laundry. According to a report, 80% of allergens are configured of mites, animal hair and pollens.

To achieve these objects and other advantages and in accordance with the purpose of the invention, as embodied and broadly described herein, a controlling method of a laundry machine includes a tiny-creatures-killing step of supplying seam to a drum to make laundry exposed to a hot environment at or over a temperature and for or over a duration of time, wherein the temperature and the duration are predetermined enough to kill tiny creatures on the laundry; a rinsing step of rinsing the laundry; and a spin-drying step of spin-drying the rinsed laundry.

In the tiny-creatures-killing step, the laundry inside the drum is exposed to an environment at or over the preset temperature for or over the preset duration to kill mites on the laundry.

For that, steam is supplied to the drum. Although steam is used in the conventional laundry machine to soak or sterilize laundry, enough steam is not supplied to efficiently kill mites.

Hot air may be used to kill mites and thus air may be heated and supplied to the drum.

However, air has a smaller heat capacity than steam and air has a mechanism that supplies heat to the laundry by heat-transfer, which is less efficient.

Since steam contains $H_2O$, steam has a larger heat capacity than air. In addition, steam has a mechanism that is absorbed in the laundry to directly supply heat to the laundry, which is substantially more efficient. That is, steam is more efficient and direct than hot air, because steam itself is a media of heat-transfer.

If hot air and steam each having an identical temperature contacts with human skin, human skin may get a burn by steam and not by hot air, which is caused by the above difference between steam and hot air.

Hot air may not directly supply heat to the laundry and may supply heat by means of its heat-transfer mechanism.

As a result, hot air takes much time to kill mites. While, steam may be directly absorbed in the laundry and killing of mites can be performed directly as well as quickly.

On the other hand, mites may be killed by only using hot water. Using only hot water over a preset temperature is not efficient in a view of energy.

For example, comparing that one liter of water is supplied as steam to kill mites, if only hot water is used, water several times as much is necessary to gain the identical effect of tiny-creatures-killing.

If the amount of the used water is larger, the amount of energy needed to make hot water is larger, too.

Steam can increase the temperature inside the drum quickly as well as directly, compared to hot water. FIG. 2 is a graph illustrating temperature differences inside the drum according to the durations between cases of supplying steam to the drum and supplying hot water to the drum.

In addition, steam can supply heat to the laundry inside the drum more uniformly than hot water, according to the result of shooting taken by an infrared ray camera, temperature uniformity of laundry is better when using steam than when using hot water.

As a result, if steam is used in comparison of hot water, the tiny-creatures-killing is performed uniformly as well as quickly.

As mentioned above, an efficient tiny-creatures-killing rate can be gained by using steam rather than hot water. However, the present invention does not exclude that the hot water and steam are used together. It is meaningful that steam is used to kill mites, and water may be used together with steam depending on cases.

Steam may be continuously supplied in the tiny-creatures-killing, or may be repeatedly supplied and stopped.

Here, it is preferable that the temperature in the killing step is 55~60° C. The duration taken for the killing is over 10 minutes. It has proved that almost 100% of allergens including mites are killed if they are exposed to a tiny-creatures-killing temperature for more than 10 minutes.

The duration and temperature for the tiny-creatures-killing may be variable based on a rate of the killing. The tiny-creatures-killing duration and temperature may be relatively varied to gain an identical degree of tiny-creatures-killing rate. For example, if the tiny-creatures-killing temperature is higher, the tiny-creatures-killing duration may be shorter. Specifically, if the tiny-creatures-killing temperature is 80° C., the tiny-creatures-killing duration may be shorter in comparison of the tiny-creatures-killing temperature of 60° C. Also, the duration and the temperature may be predetermined to gain 100% of tiny-creatures-killing rate.

If the laundry is washed by using wash water of 30° C. and wash water of 40° C., respectively, in an examination for the present invention, each of tiny-creatures-killing rate is 6.4±2.0% and 9.3±1.6%. If steam is used to make an ambient temperature inside the drum over 55° C., a tiny-creatures-killing rate is 100%.

A controlling method to satisfy the required tiny-creatures-killing temperature and duration is to supply steam for a preset duration. The designer may identify whether a required condition for the tiny-creatures-killing is satisfied based on a steam supply duration through experiments. As a result, the designer can design a controller of a laundry machine to satisfy the required condition, considering the duration of supplying steam. Here, to supply steam for the preset duration, a heater of a steam generator may be controlled to be switched off until a predetermined duration is reached.

Another aspect of a controlling method to make a condition for mites to be exposed to an environment at or over a tiny-creatures-killing temperature for or over a tiny-creatures-killing duration is to supply steam until an ambient temperature or water temperature inside the tub reaches the preset temperature, for example, 55~60° C. To supply steam for the ambient or water temperature inside the tub to reach a preset temperature, a heater of a steam generator is controlled to be switched off until the preset temperature is reached.

The controller of the laundry machine may be designed to check the tiny-creatures-killing duration and the tiny-creatures-killing temperature. Alternatively, the designer may design a tiny-creatures-killing process to satisfy such tiny-creatures-killing duration and tiny-creatures-killing temperature and design a controller to check whether an ambient or water temperature inside a tub reaches a preset temperature. That is, in the latter case, the controller is designed to check only whether the ambient or water temperature reaches the preset temperature. Thus, if the preset temperature is reached by the control of the controller, the required conditions of the tiny-creatures-killing duration and the tiny-creatures-killing temperature are satisfied.

In the meantime, since the drum is rotated during the washing, it may not be easy to measure an ambient temperature inside the drum. Thus, a temperature sensor may be provided in the tub to measure the ambient or water temperature inside the drum. Alternatively, means to directly measure a temperature inside the drum may be provided to control an amount of steam supply.

When water is not supplied to the tub enough for the temperature sensor to be submerged, the temperature sensed by the temperature sensor may be the ambient temperature. If the temperature sensor is submerged in the water, the temperature sensed by the temperature sensor may be a water temperature.

The tiny-creatures-killing step may includes supplying water to the tub until a preset water level is reached and supplying steam to the drum until an ambient or water temperature inside the tub reaches the preset temperature.

The supplying of water and the supplying of steam may be overlapped. For example, after water is supplied to the tub primarily, steam may be supplied during the secondary gradual supply of water up to the preset water level. Here, in the supplying of the water, it is preferable that the water is hot water.

Alternatively, the steam may be supplied after the supplying of water has been completed.

Detergent may be supplied in the supplying of water, together with the water and thereafter the drum is rotated. At this time, it is preferable that the detergent contains protease and that the drum is rotated even during the tiny-creatures-killing step.

House dust mites are not easily separated from the laundry when alive, because they grab the laundry in their suckers and claws. But, dead house dust mites are relatively easily separated from the laundry. The mites may be decomposed by the protease in a size of 1/100~1/10000. The protease is activated better at a range of 50~60° C.

After steam is supplied until the ambient or water temperature inside the tub reaches the preset temperature, the drum may be continuously rotated to continue the washing and to secure an enough time for the killing. However, if, by the time the preset temperature is about to be reached, the temperature and the duration for the killing are already secured to gain a wished tiny-creatures-killing rate, a further time for tiny-creatures-killing is not needed.

For example, after the detergent and water are supplied until a water level inside the tub reaches a preset level, steam is supplied to the drum until the ambient or water temperature inside the tub reaches the preset temperature of 60° C. Hence, washing is continuously performed with the rotation of the drum until the preset duration is reached. Here, after the supplying of steam is complete, the temperature inside the drum increases gradually. Here, it should be noticed that, the laundry, during a predetermined time period after the preset temperature of 60° C. is reached, is exposed to the environment over a tiny-creatures-killing temperature over a tiny-creatures-killing duration. Also, an overall duration can be predetermined to perform a series of processes including the supplying of water, the supplying of steam and the rotation of drum. For example, the overall duration may be predetermined as a tiny-creatures-killing and washing duration. Or, the overall duration may be predetermined as washing duration. Such predetermined duration may be displayed outside, which is similar to the conventional laundry machine having a preset washing time displayed outside.

In addition, the preset temperature of 60° C. may be changed into a temperature over or below the preset temperature. The preset temperature is an example of a controlling method to gain the required tiny-creatures-killing temperature and duration.

The amount of steam supplied in the tiny-creatures-killing step or the time of steam supply is determined based on the amount of laundry. In case of the above two controlling methods, the time of steam supply or the preset temperature may be variable based on the amount of laundry. Once the laundry is loaded, the controller senses the amount of laundry and determines the amount of steam and the time of steam supply. For example, if the amount of laundry is large, the time of steam supply may be longer or the preset temperature may be higher. Here, the amount of laundry may be inputted by a user or measured by a laundry amount sensor provided in the laundry machine.

By the way, wash water inside the tub may be circulated by using a circulating pump in a state that enough water is held in the tub. If the water inside the tub is high temperature water, mites may be additionally killed by the circulating water and the circulation of water is good in enhancing washing efficiency.

After the tiny-creatures-killing step is complete, the rinsing and spin-drying step are performed.

In the rinsing step, rinsing the laundry with the water supplied by the rotating of drum may be performed more than 3~4 times or more.

Commonly, the rinsing of laundry is performed two times in the rinsing step of the conventional laundry machine and such rinsing is not enough to separate mites, animal hair and pollens from the laundry.

As the number of the rinsing increases, the effect of removing allergens is enhanced. Even when the rinsing of laundry is performed two times after killing mites by using steam, the effect of removing allergens is good but not enough to remove most of allergens, compared to the effect when the rinsing is performed four times.

Especially, sample cloth contaminated by pollen protein is washed and remaining pollen protein is measured based on the number of rinsing. According to the measurement, the best result is gained when the rinsing of laundry is performed four times.

On the other hand, the drum may be rotated at a speed over 800 rpm in the spin-drying step.

The controlling method of the present invention may further include receiving a selection of an allergy care course from a user.

Like the conventional laundry machine having a course selection means for allowing a user to select courses such as a bed course and standard course, the laundry machine according to the present invention may include a course selector configured to allow a user to select an allergy course.

The tiny-creatures-killing step by using steam may be performed together with the washing step. Alternatively, after the tiny-creatures-killing step is complete, detergent and water may be supplied and thereafter the washing step may be performed.

Advantageous Effects

The present invention has an advantageous effect of removing allergens including house dust mites, animal hair and pollens efficiently.

In addition, if the house dust mites are killed by using steam, energy efficiency is high and an effect of tiny-creatures-killing is great.

DESCRIPTION OF DRAWINGS

The accompanying drawings, which are included to provide further understanding of the disclosure and are incorporated in and constitute a part of this application, illustrate embodiments of the disclosure and together with the description serve to explain the principle of the disclosure.

In the drawings:

FIG. 1 illustrates a conventional drum type washer;

FIG. 2 illustrates temperature variation based on the time inside the drum in case of using steam and hot water;

FIG. 3 illustrates an embodiment of a controlling method of a laundry machine according to the present invention;

FIG. 4 illustrates another embodiment of the controlling method according to the present invention;

FIG. 5 illustrates a further embodiment of the controlling method according to the present invention;

FIGS. 6 and 7 illustrate a still further embodiment of the controlling method according to the present invention, respectively;

FIG. 8 illustrates another still further embodiment of the controlling method according to the present invention; and FIGS. 9 and 10 illustrate an experimental result from one of the embodiments according to the present invention.

BEST MODE

Reference will now be made in detail to the specific embodiments of the present invention, examples of which are illustrated in the accompanying drawings. Wherever possible, the same reference numbers will be used throughout the drawings to refer to the same or like parts.

FIG. 3 is a block view illustrating an embodiment of a controlling method of a laundry machine according to the present invention.

In this embodiment, an allergy care course is programmed in a controller. Once a user selects the allergy care course, the controller controls the laundry machine to perform that course.

In the laundry machine is provided a course selector (not shown) for a user to select the allergy care course. Once the user selects the allergy care course through the course selector, the course selector transmits a signal to the controller.

The allergy care course of this embodiment includes a tiny-creatures-killing step S20, a washing step S30, a rinsing step S40 and a spin-drying step S50.

In the tiny-creatures-killing step S20, the controller operates the steam generator provided in the laundry machine to supply steam to the drum. Here, the duration of the tiny-creatures-killing step S20 is predetermined and steam is supplied to the drum for the preset duration.

Meanwhile, the controller may sense the amount of laundry, before performing the allergy care course and conditions for each step of the allergy care course may be determined based on the result of sensing the amount of laundry.

For example, a steam supply time in the tiny-creatures-killing step may be determined based on the laundry amount.

While steam may be supplied continuously during the tiny-creatures-killing step S20, the steam supply may be performed repeatedly with intervals.

In this embodiment, steam is supplied for about 10 minutes.

Hence, the drum is rotated during the tiny-creatures-killing step S20 and thus the laundry is tumbled so that steam is supplied uniformly to the laundry.

Once the tiny-creatures-killing step S20 is complete, the controller performs the washing step S30 in which detergent and water are mixedly supplied to perform washing. For that, the controller controls a water supply valve to allow the wash water to be supplied to the tub together with the detergent provided in a detergent box.

The detergent held in the detergent box is a kind of detergent that contains protease.

The protease breaks down the mites killed in the tiny-creatures-killing step S20. At this time, the supplied wash water is warm water at 50~60° C., which results in activating the protease enough to facilitate breaking down the mites.

Even in the washing step S30, the controller controls the steam generator to supply steam to the drum. Washing and proteolytic activities are performed efficiently, because the steam heightens an ambient temperature inside the drum.

The mites killed in the washing step S30 are separates from the laundry and the separated mites are discharged from the laundry machine together with the water.

After the washing step S30, the controller performs the rinsing step S40. For that, the controller controls the water supply valve to supply water to the drum and the motor to rotate the drum.

Here, a process of rinsing after supplying water to and rotating the drum is performed more than 4 times in the rinsing step S40.

The allergens are separated from the laundry and discharged outside in the rinsing step S40.

After the rinsing step S40, the spin-drying step S50 starts. The controller operates the motor to rotate the drum at a high speed. Here, the rotational speed of the drum is controlled over 800 rpm.

FIG. 4 illustrates another embodiment of the present invention.

In the embodiment shown in FIG. 4, between the tiny-creatures-killing step S20 and the washing step S30 there is further included a step of supplying high temperature water to the drum and rotating the drum S21 and the other configurations are identical to the embodiment shown in the FIG. 3.

After the tiny-creatures-killing step S20, the hot water of about 55~60° C. is supplied to the drum to perform a secondary tiny-creatures-killing and the drum is rotated to tumble the laundry. Hence, the allergens are separated from the laundry and the allergens are discharged outside with the water in the step S21.

Most of the mites are killed in the tiny-creatures-killing step S20 and remaining mites that might survive the tiny-creatures-killing step S20 are additionally killed by the hot water.

On the other hand, FIG. 5 illustrates a further embodiment of the present invention.

In this embodiment, between the tiny-creatures-killing step S20 and the washing step S30 there is further included a soaking step S22, unlike the above embodiment shown in FIG. 3.

In the soaking step S22, water is supplied and steam is supplied, too. The water may be hot water.

The laundry is soaked in the soaking step S22 and washing efficiency in the washing step S30 may be improved.

On the other hand, FIG. 6 illustrates a still further embodiment of the present invention.

In this embodiment, once a user selects the allergy care course and pushes a 'start' button of the laundry machine, the controller performs the allergy care course memorized therein as a program.

First, the controller controls the water supply valve to supply water to the tub. At this time, the water is supplied via the detergent box and detergent is supplied to the tub together with the water. If it is identified that the water inside the tub reaches a preset water level by using the water level sensor of the tub, the water supply valve is closed and the water supply is complete.

Hence, the controller controls the steam generator to supply steam to the drum. The time for the steam to be supplied to the drum may be preset corresponding to the time for the water supply to be complete. Alternatively, the steam may be supplied during the water supply or the steam may be supplied for a preset duration after the water supply is complete.

For the steam supply, the controller controls the water supply valve installed at the water supply line of the steam generator to supply water to the steam generator. Hence, the controller operates the heater mounted in the steam generator to boil the water. If the preset duration passes after the heater is turned on, steam is generated in the steam generator and supplied to the drum. Here, considering the time taken for the steam to be generated and supplied to the drum, the designer presets an operational time of the water supply valve and the heater for the steam generator.

The steam generator of the present invention may be varied in any types. For example, the steam generator may be a kind of a type in which a predetermined amount of water is supplied to a case and the water is boiled to generate steam (that is called as case heating type steam generator) and it may be a kind of a type in that water flowing in a pipe is heated rapidly to generate steam (that is called as pipe heating type steam generator). The pipe heating type steam generator generates steam by an operation of a heater while water is supplied through the pipe.

As shown in FIG. 6, the steam is supplied continuously until the water temperature inside the tub reaches 60° C. A temperature sensor is provided at a lower portion of the tub to sense the temperature of water.

If the temperature of wash water reaches 60° C., the controller switches off the heater to finish the steam supply.

Here, after the heater is switched on, the heater may maintain the on-state until the preset temperature of 60° C. is reached. Alternatively, to supply steam separately more than two times, the heater may maintain the on-state and switched off for a preset duration before being switched on again. That is, if steam is supplied continuously until the preset temperature is reached, the heater is maintained the on-state. If steam is supplied separately many times, the heater is controlled on and off repeatedly. This control of the heater may be applicable to the other embodiments.

If a capacity of the steam generator is small, water is supplied to the steam generator and the preset temperature may not be reached even when all of the supplied water is used. As a result, the steam generator might be operated several times in this case. That is, after water is supplied to the steam generator one time and the heater is switched on to generate and supply steam, the heater is switched off to re-supply water to the steam generator and the heater is switched on. This process may be repeated several times. At this time, it may be applicable to other embodiments that use the steam generator several times in the tiny-creatures-killing step.

Hence, tiny-creatures-killing and washing are performed continuously, with the drum being operated until the preset time passes. In this embodiment, the preset time is a washing performance time, in other words, a washing time which is configured of the allergy care course. Also, in this embodiment, the washing step includes a tiny-creatures-killing step. Hence, as the washing step being performed, tiny-creatures-killing and washing are performed together.

The tiny-creatures-killing process and washing process according to this embodiment will be explained again through FIG. 7.

As shown in FIG. 7, the steam supply is performed until the water temperature reaches 60° C. The tiny-creatures-killing is performed for a preset duration before and after the temperature of water reaches 60° C. Here, the duration is a tiny-creatures-killing time and it is for 10 minutes in this embodiment. During the tiny-creatures-killing duration, the laundry inside the drum is exposed to the tiny-creatures-killing temperature or over. As a result, even after the steam supply is complete, the drum is operated until the tiny-creatures-killing time passes. Once the preset time reaches a washing time t1, wash water is discharged and washing is complete.

According to this embodiment, once washing is complete, rinsing and spin-drying start like in the above embodiment. In this embodiment, the rinsing of laundry is performed four times in the rinsing step and thereafter the spin-drying is performed.

FIG. 8 illustrates another still further embodiment of the present invention. If the allergy care course is selected, wash water is supplied to the tub to perform washing. The washing is performed for a preset duration and steam may be supplied at this time.

Once the washing is complete, rinsing starts. Even in this embodiment, the rinsing of laundry is performed four times in the rinsing step. When spin-drying is complete, the process is complete.

In this embodiment, tiny-creatures-killing may be used if it is not necessary. After performing the conventional washing and the four times of rinsing, allergens may be removed efficiently.

The allergy care course is inputted in the controller as a program in the above embodiments. As a result, if a user only selects the allergy care course through the course selector, the controller performs the allergy care course according to the program. However, it may be varied in the present invention. Specifically, a user may select each process configured of a course. A control condition for each process is inputted in the controller and the user selects each process to configure the allergy care course. Here, some of the control conditions may be changed by the user.

One of the laundry machines presented in the present invention is a laundry washer including the steam generator shown in FIG. 1 and the allergy care course explained in the above embodiments is memorized in the controller as a program.

Here, the course selector may be further provided for the user to select the allergy care course.

If the allergy care course is selected through the course selector, the controller controls the steam generator and the water supply valve to drive the drum and the like, to perform the allergy care course.

In the meantime, experiments have been performed to confirm effects of removing allergens in the allergy care course. The experiments have been performed under the instruction of Professor Jean Emberlin at National Pollen & Aerobiology Research Unit of University of Worcester. The experiments were performed three times repeatedly and examined each amount of allergens on both of sample cloth that is washed in the allergy care course and sample cloth that is not washed in the allergy care course. The results of the experiments are shown in FIGS. 9 and 10. As shown in FIGS. 9 and 10, the amount of cat allergens and birch pollen allergens are detected below a value detectable by detection means. FIGS. 9 and 10 also show the result of examination for the sample cloth that is not washed.

The results of the experiments have proved the effect of reducing the amount of the allergy care course, which gains a certificate for allergen.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

INDUSTRIAL APPLICABILITY

The present invention has a following industrial applicability. According to the present invention, main allergens including house dust mites, animal hair and pollens may be removed efficiently. In addition, since it can kill house dust mites by using steam, the present invention has high energy efficiency and a great tiny-creatures-killing effect.

The invention claimed is:
1. A controlling method of a laundry machine comprising:
 washing laundry, the washing laundry including:
  supplying wash water to a tub for washing laundry;
  a mite-killing step of making an environment inside a drum by supplying steam into the drum until an ambient temperature or a water temperature inside the tub reaches a preset temperature to make laundry exposed to a mite-killing temperature at, and for or over a preset duration of time, the mite-killing step being performed after the wash water supplying; and
  driving the drum until a preset washing time is reached after the supplying of the steam is complete,
 wherein the mite-killing is performed for the preset duration of time before and after the ambient temperature or water temperature reaches the preset temperature.

2. The controlling method of claim 1, wherein the supplying water to the tub is performed until the water reaches a preset water level.

3. The controlling method of claim 2, wherein the supply of the steam is performed after the supplying of water is complete.

4. The controlling method of claim 2, wherein detergent is supplied to the tub together with the water.

5. The controlling method of claim 4, wherein the mite-killing step further includes:
circulating the water inside the tub by using a circulation pump.

6. The controlling method of claim 4, wherein the water inside the tub is discharged after the driving the drum.

7. The controlling method of claim 4, wherein the detergent contains protease.

8. The controlling method of claim 1, wherein the washing laundry further includes:
rinsing laundry after the washing laundry; and
spin-drying the rinsed laundry.

9. The controlling method of claim 8, wherein the drum is rotated at a speed of or over 800 rpm during the spin-drying step.

10. The controlling method of claim 8, wherein, in the rinsing the laundry, a process comprising supplying water into the tub, tumbling the laundry, and draining the water is performed more than four times.

11. The controlling method of claim 1, wherein hot water is supplied to the tub during the supplying of water.

12. The controlling method of claim 1, wherein the preset ambient temperature or water temperature is 60° C.

13. The controlling method of claim 1, wherein the mite-killing temperature is 55° C. or over 55° C., and the preset duration of time is 10 minutes or over 10 minutes.

14. A controlling method of a laundry machine comprising:
receiving a selection of an allergy care course from a user;
a mite-killing step of making an environment inside a drum by supplying steam into the drum until an ambient temperature or a water temperature inside the tub reaches a preset temperature to make laundry exposed to a mite-killing temperature at, and for or over a preset duration of time, the mite-killing step including driving the drum until a preset time is reached after the supplying of the steam is complete;
supplying wash water to the tub for washing laundry after the mite-killing step;
washing the laundry using the wash water;
rinsing the washed laundry; and
spin-drying the rinsed laundry,
wherein the mite-killing step is performed for the preset duration of time before and after the ambient temperature or water temperature reaches the preset temperature.

15. The controlling method of claim 14, wherein detergent and the wash water are mixedly supplied to a tub to perform the washing.

16. The controlling method of claim 15, wherein the supplied wash water is warm water at 50~60° C.

17. The controlling method of claim 14, further comprising a secondary mite-killing step of supplying hot water of about 55~60° C. and rotating the drum to tumble the laundry after the mite-killing step and before the washing laundry.

18. The controlling method of claim 14, further comprising soaking the laundry of supplying wash water and steam after the mite-killing step and before the washing laundry.

19. The controlling method of claim 14, further comprising supplying wash water to a tub for washing laundry, wherein the mite-killing step is performed after the wash water supplying.

20. The controlling method of claim 14, wherein the mite-killing temperature is 55° C. or over 55° C., and the preset duration of time is 10 minutes or over 10 minutes, and
wherein the preset ambient temperature or water temperature is higher temperature than the mite-killing temperature.

* * * * *